United States Patent [19]
Lo et al.

[11] Patent Number: 5,993,419
[45] Date of Patent: Nov. 30, 1999

[54] SAFETY SYRINGE

[75] Inventors: Pi-Chang Lo; Chuan-Chen Luo, both of Taipei, Taiwan

[73] Assignee: Pi-Chang Lo and Hui-Lin Tsao, Taipei, Taiwan

[21] Appl. No.: 09/212,419

[22] Filed: Dec. 16, 1998

[51] Int. Cl.$^6$ .................................................. A61M 5/00
[52] U.S. Cl. ........................................ 604/110; 604/195
[58] Field of Search .................................. 604/110, 195, 604/198, 218, 263, 187

[56] References Cited

U.S. PATENT DOCUMENTS

| | | | |
|---|---|---|---|
| 4,950,241 | 8/1990 | Ranford | 604/110 |
| 5,000,738 | 3/1991 | La Vallo et al. | 604/195 X |
| 5,088,987 | 2/1992 | Noonan, Jr. | 604/195 |
| 5,531,705 | 7/1996 | Alter et al. | 604/195 |

*Primary Examiner*—John D. Yasko
*Attorney, Agent, or Firm*—Bacon & Thomas, PLLC

[57] ABSTRACT

A safety syringe includes a barrel having a front neck, a needle holder mounted in the front neck of the barrel to hold a needle unit outside the front neck of the barrel, the needle holder having a rear coupling hole, a plunger reciprocated in the barrel, and a coupling member connected to the plunger, the coupling member having a conical split head, which is forced into engagement with the rear coupling hole of the needle holder for enabling the needle holder and the needle unit to be carried backwards with the plunger and received inside the barrel after the use of the syringe.

5 Claims, 3 Drawing Sheets

SAFETY SYRINGE

BACKGROUND OF THE INVENTION

The present invention relates to syringes, and more particularly to a safety syringe which enables the needle to be received inside the barrel after the use of the syringe.

A safety syringe allows the user (the nurse or surgeon) to pull the needle backwards to the inside of the barrel after the use of the syringe. If the needle of a syringe is kept on the outside of the barrel after its use, the needle of the syringe may injure the person who handles waste medical instruments accidentally. Such safety syringes are disclosed in Taiwan Pat. No. 253192 and No. 332433. However, these safety syringes are still not satisfactory in function. During injection, when the plunger is pushed forwards into engagement with the needle, vibration will be caused and a patient will feel pain. In addition, the needle can not be disassembled. Therefore, it is necessary to have a improved design for a safety syringe which can reduce the vibration during the engagement of a needle and a plunger.

SUMMARY OF THE INVENTION

The present invention provides a safety syringe which eliminates the aforesaid problems. It is one object of the present invention to provide a safety syringe which enables the needle unit to be pulled backwards with the plunger and received inside the barrel after the use of the syringe. It is another object of the present invention to provide a safety syringe which does not causes the obvious vibration during the engagement of a needle and a plunger. It is still another object of the present invention to provide a safety syringe which has a detachable needle unit that can easily be installed. To achieve these and other objects of the present invention, there is provided a safety syringe comprised of a needle unit, a barrel, a needle holder, a plunger, and a coupling member. The barrel comprises a front neck. The needle holder is mounted in the front neck of the barrel to hold the needle unit outside the front neck of the barrel. The needle holder has a rear coupling hole. The coupling member is integral with the plunger, having a conical split head, which is forced into engagement with the rear coupling hole of the needle holder for enabling the needle holder and the needle unit to be carried backwards with the plunger and received inside the barrel after the use of the syringe. When the plunger is pushed forwards to the front side in the barrel, the conical split head is compressed inwards by the periphery of the rear coupling hole of the needle holder, and allowed to be forced through the rear coupling hole into the chamber inside the needle holder. When passed through the rear coupling hole of the needle holder, the conical split head immediately returns to its former shape, and becomes stopped inside the needle holder, for enabling the needle holder to be moved backwards with the plunger. The split design of the split head of the coupling member enables the coupling member to be easily coupled to the rear coupling hole of the needle holder without causing a vibration.

DETAILED DESCRIPTION OF THE PREFERRED EMBODIMENT

Figure 1:
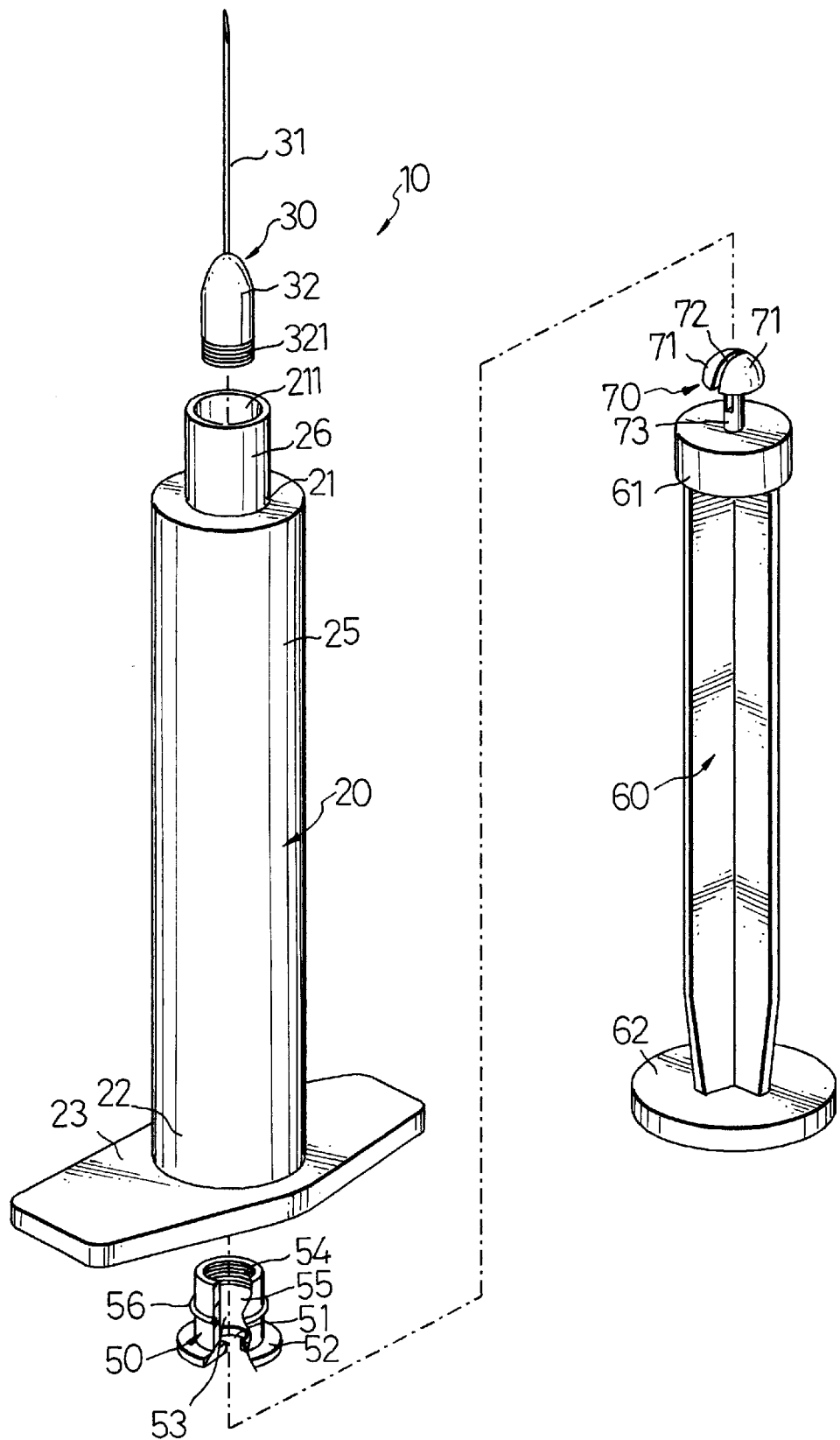
FIG. 1 is an exploded view of a safety syringe according to the present invention.

Referring to Figures from 1 through 5, a safety syringe 10 is shown comprised of a barrel 20, a needle unit 30, a needle holder 50, a plunger 60, and a coupling member 70.

The needle unit 30 comprises a needle cannula 31, and a hollow needle base 32. The needle cannula 31 has one end integral with one end of the hollow needle base 32. The needle base 32 has an outer thread 321 at one end remote from the needle cannula 31.

The barrel 20 comprises a cylindrical body 25 with a receiving chamber 24, a neck 26 axially forwardly extended from the front end 21 of the body 25 and defining a front opening 211, a shoulder 261 formed at the front end 21 between the neck 26 and the body 25, a rear opening 221 defined within the rear end 22 of the body 25 remote from the neck 26 and disposed in communication with the receiving chamber 24, and a finger flange 23 raised from the rear end 22 of the body 25 around the rear opening 221.

The needle holder 50 is a hollow cylindrical member comprising a front hole 55 at a front end thereof, a rear coupling hole 51 at a rear end thereof, a chamber 53 in communication between the front hole 55 and the rear coupling hole 51, an inner thread 54 provided in the front hole 55 for engagement with the outer thread 321 of the needle base 32 of the needle unit 30, and an outward stop flange 52 raised around the periphery at the rear end. When the needle holder 50 is inserted through the rear opening 221 into the barrel 20, it is pushed forwards to the front end 21 of the body 25 of the barrel 20 and engaged into the neck 26 of the barrel 20, permitting the outward stop flange 52 to be stopped inside the barrel 20 against the shoulder 261. Further, an O-ring 56 is mounted around the needle holder 50 to seal the gap between the outside wall of the needle holder 50 and the inside wall of the neck 26. After installation of the needle holder 50 in the neck 26, the needle unit 30 is fastened to the needle holder 50 by threading the outer thread 321 of the needle base 32 into the inner thread 54 of the needle holder 50.

The plunger 60 comprises a stopper 61 at its front end, and a thumb rest 62 at its rear end. When the plunger 60 is inserted through the rear opening 221 into the barrel 20, the stopper 61 is disposed in close contact with the inside wall of the body 25.

The coupling member 70 is provided at the front side of the stopper 61 of the plunger 60, comprising a conical split head 71 and a neck 73. The neck 73 is integral with the front side wall of the stopper 61 of the plunger 60. The conical split head 71 is integral with one end of the neck 73 remote from the stopper 61, having a split 72 on the middle, which separates the conical split head 71 into two symmetrical halves. The diameter of the conical split head 71 gradually reduces from the rear side (the side to which the neck 73 is connected) toward the front side (the side remote from the neck 73). The cross section of the rear side of the conical split head 71 is larger than the rear coupling hole 51 of the needle holder 50.

Figure 2:
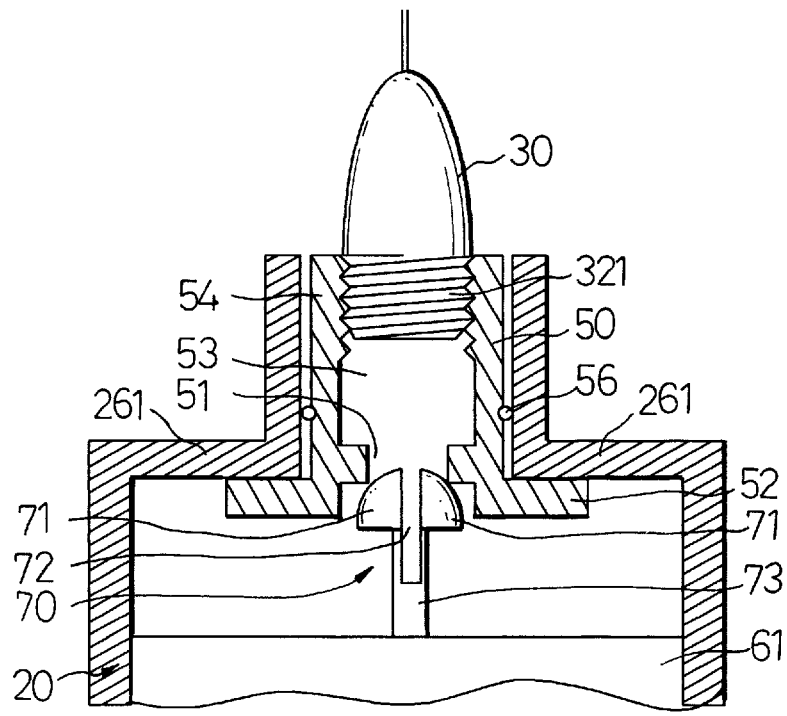
FIG. 2 is a sectional view of a part of the present invention, showing the coupling member moved to the rear side of the needle holder.
Figure 3:
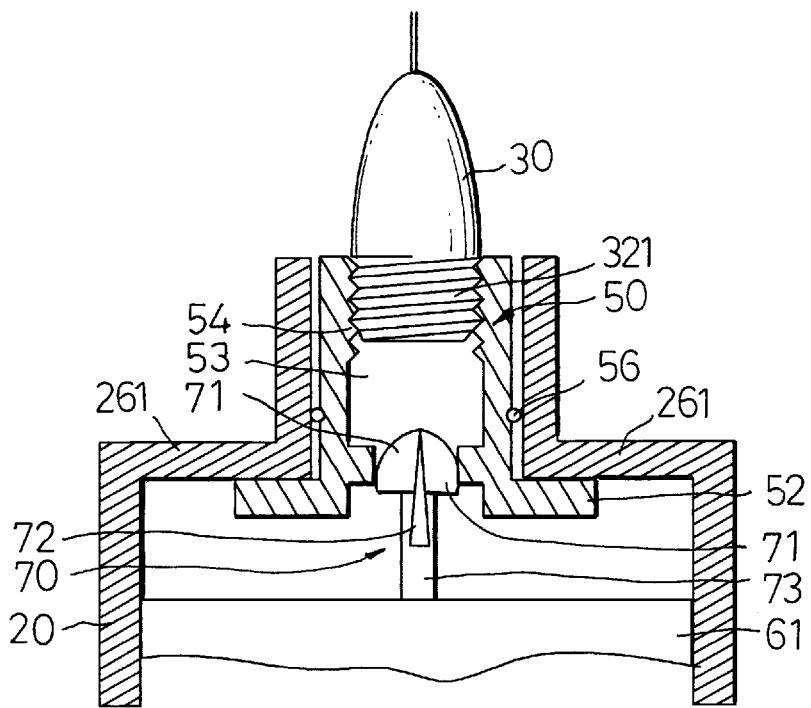
FIG. 3 is similar to FIG. 2 but showing the conical split head compressed and inserted into the rear coupling hole of the needle holder.
Figure 4:
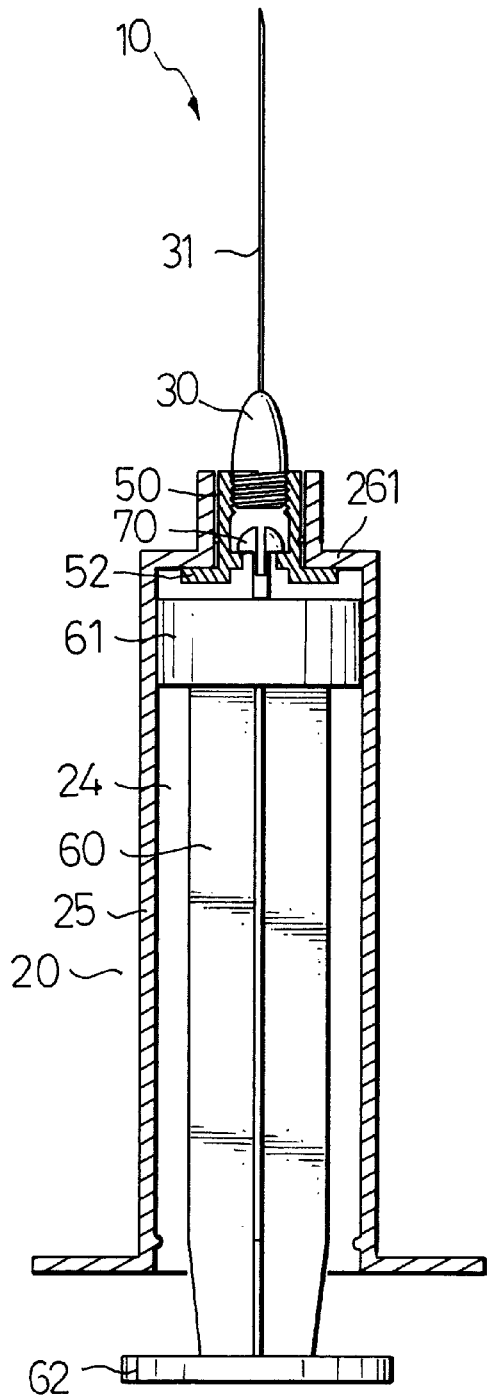
FIG. 4 is a longitudinal view in section of the present invention, showing the plunger pushed to the front side, the coupling member coupled to the needle holder.
Figure 5:
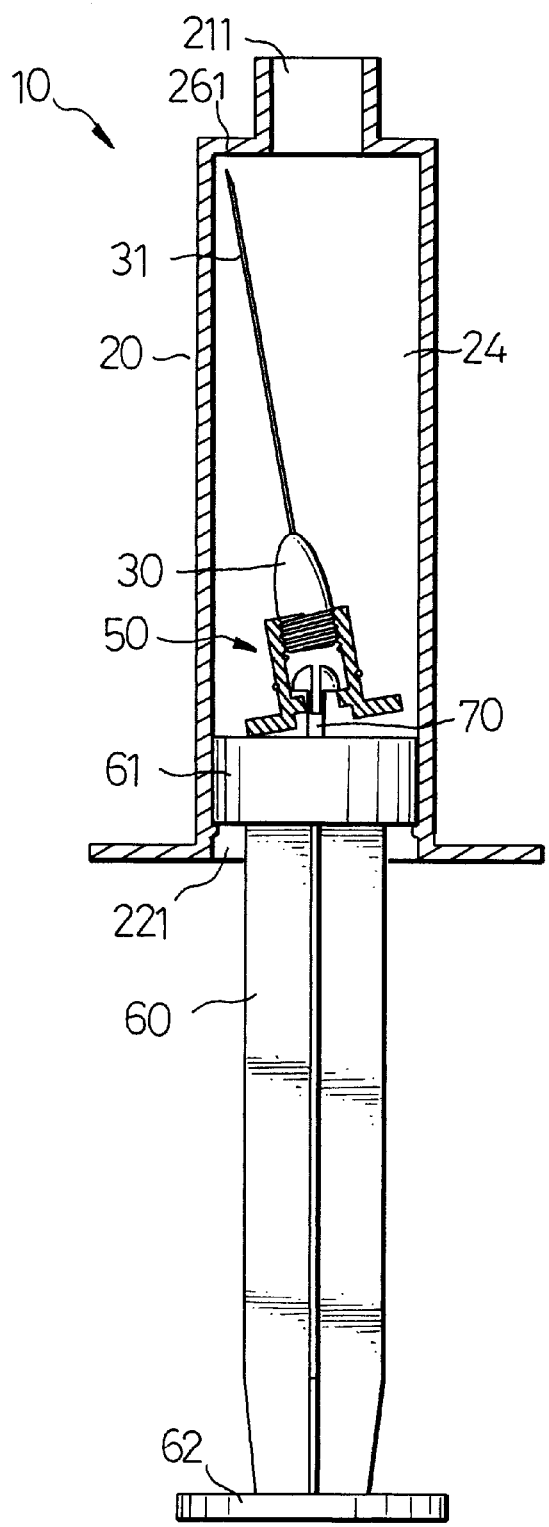
FIG. 5 is another sectional view of the present invention, showing the plunger pulled to the rear side, the needle holder received inside the barrel, the needle unit tilted on the coupling member inside the barrel.

Referring to Figures from 2 through 5 again, when the plunger 60 is pushed forwards to the front side in the barrel 20 (see FIG. 2), the conical split head 71 is compressed inwards by the periphery of the rear coupling hole 51 (see FIG. 3), and allowed to be forced through the rear coupling hole 51 into the chamber 53 inside the needle holder 50 (see FIG. 4). After passed through the rear coupling hole 51, the conical split head 71 immediately returns to its former shape, and becomes unable to be pulled backwardly out of the rear coupling hole 51, i.e., the coupling member 70 and the needle holder 50 are coupled together (see FIG. 4). When the plunger 60 is pulled backwards after the coupling member 70 and the needle holder 50 have been coupled together, the needle unit 30 is carried with the needle holder 50 by the plunger 60 backwardly to the inside of the receiving chamber 24 of the body 25 of the barrel 20 (see FIG. 5). Because the cross section of the neck 73 of the coupling member 70 is smaller than the diameter of the rear coupling hole 51 of the coupling member 50, the needle unit 30 tilts on the coupling member 70 when received in the receiving chamber 24 inside the body 25 of the barrel 20 (see FIG. 5). At this time, the user can then pushed to the plunger 60 forwards to deform the needle cannula 31 of the needle unit 30.

While only one embodiment of the present invention has been shown and described, it will be understood that various modifications and changes could be made thereunto without departing from the spirit and scope of the invention disclosed. For example, the conical split head 71 can be made having intersected splits, that separate the conical split head 71 into more than two parts.

What the invention claimed is:

1. A safety syringe comprising:
   a barrel, said barrel comprising a cylindrical body with a receiving chamber, said cylindrical body having a front end and a rear end, a neck axially forwardly extended from the front end of said body, a shoulder connected between the neck and body of said barrel, a rear opening defined within the rear end of said body and disposed in communication with said receiving chamber, and a finger flange raised from the rear end of said body;
   a hollow cylindrical needle holder received inside said barrel and inserted into the neck of said barrel, said needle holder comprising a front hole at a front end thereof, a rear coupling hole at a rear end thereof, a chamber in communication between the front hole and rear coupling hole of said needle holder, and stopped inside said barrel against said shoulder;
   a plunger inserted through the rear opening of said barrel into the receiving chamber of said body of said barrel, said plunger comprising a stopper at a front end thereof, which is disposed in contact with an inside wall of said body of said barrel, and a thumb rest at a rear end thereof disposed outside said barrel;
   a needle unit connected to said needle holder and extended out of the neck of said barrel, said needle unit comprising a hollow needle base connected to said needle holder, and a needle cannula, said needle cannula having one end integral with one end of said hollow needle base and an opposite end extended out of the neck of said barrel; and
   a coupling member raised from the stopper of said plunger and adapted to be coupled to said needle holder for enabling said needle holder and said needle unit to be pulled backwards into the inside of said receiving chamber of said barrel by said plunger, said coupling member comprising a split head having a front side and a rear side, and a neck extended from the rear side of said split head and connected to said stopper, said split head having a diameter gradually reducing from its rear side toward its front side, the cross section of the front side of said split head being smaller than the diameter of the rear coupling hole of said needle holder, the cross section of the rear side of said split head being larger than the diameter of the rear coupling hole of said needle holder.

2. The safety syringe of claim 1 further comprising an O-ring mounted around said needle holder.

3. The safety syringe of claim 1 wherein said needle holder comprises an inner thread in the front hole thereof, and said needle base has an outer thread at one end threaded into the inner thread of said needle holder.

4. The safety syringe of claim 1 wherein said split head of said coupling member has an axially extended split, which separates said split head into two symmetrical halves.

5. The safety syringe of claim 4 wherein said split head of said coupling member has a conical shape.

* * * * *